United States Patent
Mack et al.

(10) Patent No.: US 12,036,220 B2
(45) Date of Patent: Jul. 16, 2024

(54) LYOPHILIZED ORALLY DISINTEGRATING TABLET FORMULATIONS OF d-LYSERGIC ACID DIETHYLAMIDE FOR THERAPEUTIC APPLICATIONS

(71) Applicant: Mind Medicine, Inc., New York, NY (US)

(72) Inventors: Peter Mack, Chapel Hill, NC (US); Timm Trenktrog, Binningen (CH); Dustin Melton, Melbane, NC (US); Bethany Amber Doty, Clayton, NC (US); Jon Schroeder, Madison, WI (US); Lisa Marie Garrett, Swindon (GB)

(73) Assignee: Mind Medicine, Inc., New York, NY (US)

( * ) Notice: Subject to any disclaimer, the term of this patent is extended or adjusted under 35 U.S.C. 154(b) by 0 days.

(21) Appl. No.: 18/194,761

(22) Filed: Apr. 3, 2023

(65) Prior Publication Data
US 2023/0218532 A1     Jul. 13, 2023

Related U.S. Application Data

(63) Continuation of application No. 18/077,085, filed on Dec. 7, 2022, and a continuation of application No. 17/890,133, filed on Aug. 17, 2022.

(60) Provisional application No. 63/234,773, filed on Aug. 19, 2021.

(51) Int. Cl.
| | |
|---|---|
| *A61K 31/48* | (2006.01) |
| *A61K 9/00* | (2006.01) |
| *A61K 9/20* | (2006.01) |
| *A61K 47/10* | (2017.01) |
| *A61K 47/22* | (2006.01) |
| *A61K 47/26* | (2006.01) |
| *A61K 47/36* | (2006.01) |
| *A61K 47/60* | (2017.01) |
| *A61K 47/69* | (2017.01) |

(52) U.S. Cl.
CPC ............ *A61K 31/48* (2013.01); *A61K 9/0056* (2013.01); *A61K 9/20* (2013.01); *A61K 9/2013* (2013.01); *A61K 9/2018* (2013.01); *A61K 9/205* (2013.01); *A61K 9/2054* (2013.01); *A61K 9/2095* (2013.01); *A61K 47/10* (2013.01); *A61K 47/22* (2013.01); *A61K 47/26* (2013.01); *A61K 47/36* (2013.01); *A61K 47/60* (2017.08); *A61K 47/6923* (2017.08)

(58) Field of Classification Search
None
See application file for complete search history.

(56) References Cited

U.S. PATENT DOCUMENTS

| | | | |
|---|---|---|---|
| 9,192,580 B2 * | 11/2015 | Green | A61K 9/2063 |
| 2004/0138098 A1* | 7/2004 | Fein | A61P 13/00 514/10.9 |
| 2004/0228919 A1* | 11/2004 | Houghton | A61K 39/36 424/484 |
| 2018/0036303 A1* | 2/2018 | Raz | A61K 45/06 |
| 2018/0228797 A1† | 8/2018 | Bosse | |
| 2020/0085816 A1† | 3/2020 | Raz | |
| 2020/0101041 A1† | 4/2020 | Kleidon | |
| 2021/0015738 A1† | 2/2021 | LaRosa | |
| 2021/0137908 A1† | 5/2021 | Kristensen | |

OTHER PUBLICATIONS

Bhaskar et al. "A Review on Formulation Approaches in Immediate Release Tablet," Journal of Drug Delivery & Therapeutics. 2018; 8(3): 153-161. (Year: 2018).*
Janga et al. "Photostability Issues in Pharmaceutical Dosage Forms and Photostabilization," AAPS PharmSciTech, vol. 19, No. 1, Jan. 2018. (Year: 2018).*
Pacheco et al. "A review on orally disintegrating films (ODFs) made from natural polymers such as pullulan, maltodextrin, starch, and others," International Journal of Biological Macromolecules vol. 178, May 1, 2021 (Year: 2021).*
Psychedelic Experience web page retrieved from The Wayback Machine on 4/23/3021 (Year: 2021).*
Celestino et al. "Rational use of antioxidants in solid oral pharmaceutical preparations," Brazilian Journal of Pharmaceutical Sciences vol. 48, n. 3, Jul./Sep. 2012. (Year: 2012).*
NHS, Swallowing Difficulties in Dementia, Mar. 17, 2016, NHS Hull University Teaching Hospitals NHS Trust, https://www.hey.nhs.uk/patient-leaflet/swallowing-difficulties-in-dementia/.†

* cited by examiner
† cited by third party

*Primary Examiner* — Jeffrey S Lundgren
*Assistant Examiner* — Michael J Schmitt
(74) *Attorney, Agent, or Firm* — Kohn & Associates PLLC

(57) ABSTRACT

A solid oral immediate release formulation of LSD, wherein the composition is produced by lyophilization of a feedstock in a pre-formed mold to form an orally disintegrating tablet. A method of making a solid oral immediate release formulation of LSD by lyophilizing a flash frozen stock solution of LSD and excipients, including a non-gelling matrix former, filler, and binder in a pre-formed mold, and forming an orally disintegrating tablet. A method of treating an individual by administering a solid oral immediate release formulation of LSD, wherein the composition is produced by lyophilization of a feedstock in a pre-formed mold to form an orally disintegrating tablet and treating the individual.

7 Claims, 2 Drawing Sheets

D-LSD D-Tartrate

LYOPHILIZED ORALLY DISINTEGRATING TABLET FORMULATIONS OF d-LYSERGIC ACID DIETHYLAMIDE FOR THERAPEUTIC APPLICATIONS

BACKGROUND OF THE INVENTION

1. Technical Field

The present invention relates to the formulation of drugs. More specifically, the present invention relates to an immediate release formulation for a pharmaceutical formulation of d-lysergic acid diethylamide (LSD).

2. Background Art

Oral solution formulations are convenient for studies in a small number of sites and with a limited number of patients, mainly early phase development studies, but may not be suitable for later phase development studies run in many centers and across wide geographies nor for commercialization due to challenges in product stability and supply chain, such as the potential requirement for cold chain storage.

Solid oral formulations as tablets or capsules are more common in later phase clinical development and commercially due to advantages in production, supply chain, and patient convenience. Solid oral formulations can be immediate release, dissolving instantaneously in the mouth or stomach, or extended release in which the drug release is prolonged over time.

Orally disintegrating tablets (ODTs) are another solid dosage form which is formulated with the aim of increasing the dissolution rate of a pharmaceutical product and promoting pre-gastric absorption. In order to achieve rapid disintegration rates, the ODT formulation must provide high porosity, low density, and a low hardness (Berthoumieu et al., 2010; Bandari et al., 2008). This dosage form can be chosen to modify absorption or for patient populations that have difficulty in swallowing (Lindgren et al., 1993), and is also suitable for use in geriatric and pediatric patients, or for those who suffer from conditions such as dysphagia (Sastry et al., 2000).

From the perspectives of cost and simplicity, direct compression is a common method for preparing ODTs. However, the disintegration capacity of ODTs produced in this way is limited by the size and hardness of the resulting tablets. An alternative method for preparing ODTs is freeze drying. For example, the Zydis® ODT (orally dissolving tablet) fast-dissolve formulation, is a freeze-dried oral solid dosage form that disperses almost instantly in the mouth with no water required.

LSD is derived from its German name LysergSaureDiethylamid (Lysergic acid diethylamide). Lysergide belongs to a family of indole alkylamines that includes numerous substituted tryptamines such as psilocin (the active moiety of psilocybin) and N,N-dimethyltryptamine (DMT). The IUPAC name for LSD is 9,10-didehydro-N,N-diethyl-6-methylergoline-8β-carboxamide.

LSD can be used to assist psychotherapy for many indications including anxiety, depression, addiction, personality disorder, and others and can also be used to treat other disorders such as cluster headache, migraine, and others (Passie et al., 2008; Hintzen et al., 2010; Nichols, 2016; Liechti, 2017). Effects of LSD can include altered thoughts, feelings, awareness of surroundings, dilated pupils, increased blood pressure, and increased body temperature.

Therapeutic use of LSD is showing promising results for treating various neurological and behavioral disorders. However, due to its potency there can be challenges in developing and manufacturing solid oral formulations of LSD that meet pharmaceutically acceptable limits for content uniformity and chemical stability.

Clinical studies with LSD have focused on oral solution drug product forms. There has been little to no formulation development work with LSD. Oral solutions were used historically and almost all the old studies and anecdotal data are with oral solutions or impregnated papers/cartons.

There is a need for an LSD dosage form and drug product that is both commercially attractive to a broad patient population and meets regulatory/quality expectations for suitability and robustness. A commercially viable solid oral, immediate release pharmaceutical formulation of d-Lysergic Acid Diethylamide (LSD), as a free base or in a salt form, does not currently exist as a marketed product or reported in literature. With the expected therapeutic dose of LSD to be in the 10's to 100's of micrograms, challenges exist for achieving acceptable drug content uniformity and chemical stability. Furthermore, previous studies have shown LSD in oral solution is not stable at room temperature (Holze et al 2019).

In addition to achieving a uniform and stable immediate release drug product formulation, the final drug product should be in a form that is easily administered to a broad range of patient populations, including, but not limited to the elderly, pediatrics, and patients with a condition that may limit their ability to swallow.

SUMMARY OF THE INVENTION

The present invention provides a solid oral immediate release formulation of LSD, including LSD formulations intended for an orally disintegrating tablet dosage form, wherein the composition is produced by lyophilization of a feedstock in a pre-formed mold to form an orally disintegrating tablet.

The present invention further provides a method of making a solid oral immediate release formulation of LSD by lyophilizing a flash frozen stock solution of LSD and excipients of a non-gelling matrix former, filler, binder, and buffer as well as additional excipients such as antioxidants, photostabilization agents, permeation enhancers and flavoring agents, in a pre-formed mold, and forming an orally disintegrating tablet.

The present invention also provides for a method of treating an individual by administering a solid oral immediate release formulation of LSD, wherein the composition is produced by lyophilization of a feedstock in a pre-formed mold to form an orally disintegrating tablet and treating the individual.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
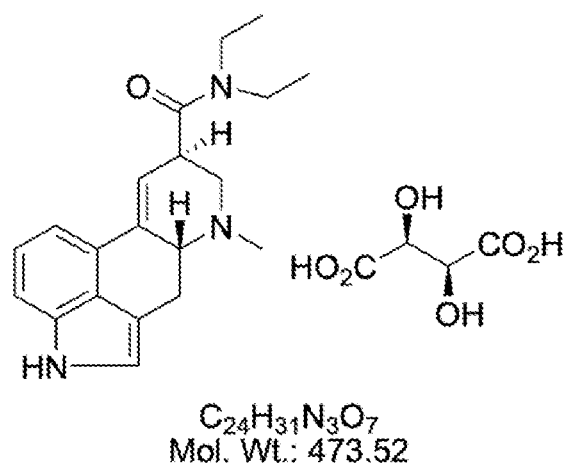
FIG. 1 is a representation of D-LSD D-tartrate salt.

The present invention provides for a solid oral formulation of LSD in a quick or immediate release dosage form such as an orally disintegrating tablet. The term "quick release tablet" is a mechanism that (similar to immediate-release dosage) delivers a drug immediately in contrast with a delay after its administration (delayed-release dosage) or for a prolonged period of time (extended-release (ER, XR, XL) dosage) or to a specific target in the body (targeted-release dosage). Preferably, it refers to minimal time dependent release in oral dose formulations. The present invention provides a composition, preferably including LSD as its active, or one of its active ingredients, that dissolve relatively quickly once orally ingested. This provides an easy to administer yet anticipated to be effective and efficacious therapeutic effect. The composition is preferably produced by lyophilization of a feedstock in a pre-formed mold to form the orally disintegrating tablet.

The LSD can be in a free base form or a salt form as a crystalline or non-crystalline solid. The salt can be, but is not limited to, hydrochloride, hydrobromide, maleate, tartrate (including D-tartrate and meso-tartrate), citrate, phosphate, fumarate, sulfate, mesylate, acetate, oxalate, benzoate, benzensulfonate, xinafoate, 1,5-Napthalene disulfonate, ascorbate, and naphthalene-2-sulfonate. The dose of LSD can preferably be 0.01-1 mg (10-1000 µg). However, dosing can be adjusted depending on indication, age, weight, and other factors affecting the pharmacology, physiology, and drug/drug interactions in a given patient.

The preferred solid oral formulation is an orally disintegrating tablet (ODT) such as using ZYDIS® (Catalent, Inc.) technology, described in U.S. Pat. No. 9,192,580 B2, which is herein incorporated by reference. This is further shown in EXAMPLE 1. Typical ZYDIS® ODT formulations include a non-gelling matrix former, filler, binder, and pH modifying agent (i.e., buffer). In addition, antioxidants, photostabilization agents, permeation enhancers, coloring agents, and sweeteners/flavoring agents can be included in ZYDIS® ODT formulations.

Examples of non-gelling matrix formers used include, but are not limited to, non-gelling gelatin (including fish gelatin), maltodextrin, modified starches, starch ethers, low molecular weight dextrans, and low to intermediate molecular weight cellulose gums (U.S. Pat. No. 10,548,839 B2).

Examples of fillers used include lactose (including anhydrous), mannitol, dicalcium phosphate, calcium sulfate, starch (starch as used herein can include dry or pre-gelled), cellulose (including microcrystalline cellulose), kaolin, sodium chloride, sorbitol, trehalose, sucrose, etc.

Examples of binders include acacia gum, methylcellulose, hydroxypropyl methylcellulose, hydroxypropyl cellulose, tragacanth, polyvinyl pyrrolidone (PVP), starch, etc.

Buffer is added to target the formulation to a specific pH. Currently, three buffers, citrate, phosphate, and acetate, make up the majority of buffers used in parenteral pharmaceuticals approved by the FDA, but less precedented excipients are certainly available to use in commercial dosage forms. The pH of a formulation alternatively can be adjusted with unbuffered acid (i.e., hydrochloric acid) or unbuffered base (i.e., sodium hydroxide).

Antioxidants can be added to the formulation in order to minimize degradation due to oxidative stress. The term oxidation can be defined as the incorporation of oxygen into the structure of a drug, or as the process of converting one chemical substance into another derivative bearing a smaller number of electrons. Examples of such antioxidants are ascorbic acid, citric acid, butylated hydroxy anisole (BHA), and butylated hydroxyl toluene (BHT).

Many drugs are sensitive to light and therefore their formulated products can degrade during manufacturing, storage, and administration. The photostability of a drug substance can be defined as the response of the drug or drug product to the exposure to solar, UV, and visible light in the solid, semisolid, or liquid state that leads to a physical or chemical change. Undo light exposure can result in potency loss, altered efficacy, and adverse biological effects. Various additives or encapsulation methods and compositions can be used to protect the active product from light in order to minimize any degradation due to light exposure (i.e., photostabilization agents).

Photo degradation can also occur in combination with oxygen exposure, resulting in photo-oxidation degradation. Some of the commonly used antioxidants to protect against photo-oxidation are ascorbic acid, α-tocopherol, butylated hydroxyanisole (BHA), butylated hydroxytoluene (BHT), L-histidine, propyl gallate, and sulfur compounds. Ascorbic acid, α-tocopherol, β-carotene, and BHT act as free radical scavengers and singlet oxygen quenchers and thus inhibit the photosensitization reactions. If a drug substance acts as a photosensitizer and initiates a chain reaction in the drug product, some of the excipients can be oxidized, while the drug can be protected from photodegradation.

The formulation can also contain permeability enhancers to increase the extent and/or rate of absorption. Examples of such enhancers are sulphoxides (such as dimethylsulphoxide, DMSO), azones (e.g., laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes.

Coloring agents, sweeteners, and flavoring agents can also be added to solid oral formulations in order to improve patient recognition and acceptability.

The compound of the present invention is administered and dosed considering the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants, and vehicles. The patient being treated is a warm-blooded animal and, in particular, mammals including man. The pharmaceutically acceptable carriers, diluents, adjuvants, and vehicles generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

Absorption of the active drug can be targeted. Drug absorption is determined by the drug's physicochemical properties, formulation, and route of administration. Dosage forms (e.g., tablets, capsules, solutions), consisting of the drug plus other ingredients, are formulated to be given by various routes (e.g., oral, buccal, sublingual, rectal, parenteral, topical, inhalational). Regardless of the route of administration, drugs must be in solution to be absorbed. Thus, solid forms (e.g., tablets, capsules) must be able to disintegrate and deaggregate. Solid oral tablets and capsule formulations typically have gastric absorption, whereas an ODT formulation can be formulated to target pre-gastric or buccal absorption which can further enhance bioavailability.

The present invention provides for a method of making a solid oral immediate release formulation of LSD, as a free base or in a salt form, by lyophilizing a flash frozen stock solution of drug and excipients (i.e., non-gelling matrix former, filler, binder, and buffer as well as optional additional excipients such as antioxidants, photostabilization agents, permeation enhancers and flavoring agents as described above) in a pre-formed mold to form an orally disintegrating tablet. This approach considers the challenges associated with formulating a low dose product while maintaining content uniformity and chemical integrity of LSD.

The present invention provides for a method of treating an individual, by administering a solid oral immediate release formulation of LSD of an orally disintegrating tablet, wherein the composition is produced by lyophilization of a feedstock in a pre-formed mold to form the orally disintegrating tablet and treating the individual.

The condition or disease being treated can include, but is not limited to, anxiety disorders (including anxiety in advanced stage illness e.g. cancer, as well as generalized anxiety disorder), depression (including postpartum depression, major depressive disorder and treatment-resistant depression), headache disorder (including cluster headaches and migraine headache), obsessive compulsive disorder (OCD), personality disorders (including conduct disorder), stress disorders (including adjustment disorders and post-traumatic stress disorder), drug disorders (including alcohol dependence or withdrawal, nicotine dependence or withdrawal, opioid dependence or withdrawal, cocaine dependence or withdrawal, methamphetamine dependence or withdrawal), other addictions (including gambling disorder, eating disorders, and body dysmorphic disorder), pain, neurodegenerative disorders (such as dementia, Alzheimer's Disease, Parkinson's Disease), autism spectrum disorder, eating disorders, or neurological disorders (such as stroke). The individual can have trouble swallowing or be elderly.

The invention is further described in detail by reference to the following experimental examples. These examples are provided for the purpose of illustration only and are not intended to be limiting unless otherwise specified. Thus, the invention should in no way be construed as being limited to the following examples, but rather, should be construed to encompass any and all variations which become evident as a result of the teaching provided herein.

EXAMPLE 1: LYOPHILIZATION OF D-LSD D-TARTRATE STOCK SOLUTION TO FORMULATE AN ORALLY DISINTEGRATING TABLET

Figure 2:
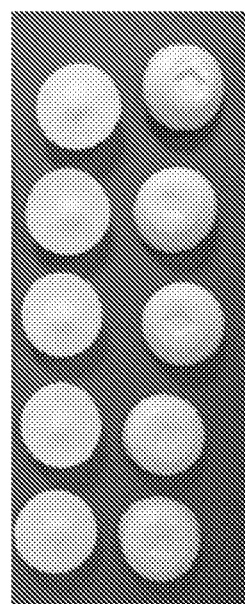
FIG. 2 is a photograph of Zydis ODT containing LSD.

Solid oral formulations of d-LSD D-tartrate in a fast dispersing orally disintegrating tablet (ODT) were produced the following method: A) Generating a formula stock solution containing d-LSD D-tartrate, a non-gelling matrix forming excipient, a filler excipient, and a binding agent fully dissolved in water; B) Dosing the stock solution in pre-formed molds; and C) Lyophilizing the dosed formulations to remove water by sublimation. Formulation compositions are provided in TABLE 1. Images for Formulation 1 are shown in FIG. 2. All formulations disintegrated in less than 60 seconds demonstrating immediate release.

TABLE 1 d-LSD D-tartrate formulations lyophilized to form orally disintegrating tablets

| Component | Formulation 1 | Formulation 2 | Formulation 3 | Approx Wt % |
|---|---|---|---|---|
| Drug | | d-LSD D-tartrate | | <1% |
| Non-gelling matrix | Fish Gelatin | Maltodextrin | | 2-10% |
| Binder | | Methylcellulose | | 1-5% |
| Filler | Mannitol | Mannitol | Trehalose | 2-10% |
| Solvent | | Water | | qs to 100% |

These formulations were protected from moisture ingress, set on stability at 40° C., and after one month tested for chemical degradation. The total chemical impurities are presented in TABLE 2. These results show minor changes in total impurities after one month stored at accelerated conditions, demonstrating the suitability of lyophilized ODT formulations of d-LSD D-tartrate.

TABLE 2

Total Impurities of lyophilized d-LSD D-tartrate formulations after one month storage at 40° C.

| Time point | Formulation 1 | Formulation 2 | Formulation 3 |
|---|---|---|---|
| T = 0 | 0.9 | 0.3 | 0.7 |
| T = 1 mo @ 40° C. | 1.6 | 0.2 | 0.5 |

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. An LSD tablet prepared by lyophilization of a stock solution in a pre-formed mold, wherein the stock solution consists essentially of:
  a non-gelling matrix former of maltodextrin at 2-10% weight percent, a binder of hydroxypropyl methylcellulose at 1-5% weight percent, a filler chosen from the group consisting of mannitol at 2-10% weight percent and trehalose at 2-10% weight percent, LSD tartrate present at less than 1% weight percent, and water; wherein
the LSD tablet is capable of disintegrating within 60 seconds.

2. A method of making an LSD tablet from a stock solution, wherein the stock solution consists essentially of:
  a non-gelling matrix former of maltodextrin at 2-10% weight percent, a binder of hydroxypropyl methylcellulose at 1-5% weight percent, a filler chosen from the group consisting of mannitol at 2-10% weight percent and trehalose at 2-10% weight percent, LSD tartrate present at less than 1% weight percent, and water; including the steps of:

flash freezing the stock solution in a pre-formed mold;

lyophilizing the flash frozen stock solution in the pre-formed mold;

and forming an orally disintegrating tablet capable of rapidly disintegrating in less than 60 seconds.

3. The method of claim 2, wherein the stock solution further comprises a buffer chosen from the group consisting of citrate, phosphate, and acetate.

4. A method of treating an individual in need thereof with LSD comprising administering an LSD tablet prepared by lyophilization of a stock solution in a pre-formed mold, wherein the stock solution consists essentially of:

a non-gelling matrix former of maltodextrin at 2-10% weight percent, a binder of hydroxypropyl methylcellulose at 1-5% weight percent, a filler chosen from the group consisting of mannitol at 2-10% weight percent and trehalose at 2-10% weight percent, LSD tartrate present at less than 1% weight percent, and water; wherein the LSD tablet is capable of disintegrating within 60 seconds;

and treating the individual.

5. The method of claim 4, wherein the individual has trouble swallowing, is elderly, or has dementia.

6. The method of claim 4, wherein said treating step is further defined as treating a condition or disease chosen from the group consisting of anxiety disorders, depression, headache disorder, obsessive compulsive disorder (OCD), personality disorders, stress disorders, drug disorders, gambling disorder, eating disorders, body dysmorphic disorder, pain, neurodegenerative disorders, autism spectrum disorder, and neurological disorders.

7. The method of claim 4, wherein said administering step is further defined as administering 0.01-1 mg of LSD.

* * * * *